United States Patent
Hollard

(10) Patent No.: US 8,641,779 B1
(45) Date of Patent: Feb. 4, 2014

(54) PROSTHETIC LIMB MOUNTING LEVER AND METHOD THEREFORE

(76) Inventor: Joseph Hollard, Covington, LA (US)

(*) Notice: Subject to any disclaimer, the term of this patent is extended or adjusted under 35 U.S.C. 154(b) by 41 days.

(21) Appl. No.: 13/267,103

(22) Filed: Oct. 6, 2011

(51) Int. Cl.
*A61F 2/80* (2006.01)
*A61B 17/56* (2006.01)

(52) U.S. Cl.
USPC ................................ 623/36; 623/27; 606/99

(58) Field of Classification Search
USPC ....................................... 623/32, 33; 606/99
See application file for complete search history.

(56) References Cited

U.S. PATENT DOCUMENTS

| | | |
|---|---|---|
| 2,666,927 A | 1/1954 | Morheiser |
| 3,922,727 A | 12/1975 | Bianco |
| 4,038,701 A | 8/1977 | McFall et al. |
| 5,203,791 A | 4/1993 | Blanchard |
| 5,211,667 A | 5/1993 | Danforth |
| 5,326,351 A | 7/1994 | Sarazin |
| 5,549,429 A * | 8/1996 | Sergent ............................. 410/96 |
| 5,658,353 A | 8/1997 | Layton |
| 5,888,232 A | 3/1999 | Taylor |
| 6,666,894 B2 | 12/2003 | Perkins et al. |
| 6,793,682 B1 | 9/2004 | Mantelmacher |
| 6,797,008 B1 | 9/2004 | Arbogast et al. |
| 7,389,971 B2 | 6/2008 | Gaudreault et al. |
| 7,842,099 B2 | 11/2010 | Mantelmacher |
| 7,850,739 B2 | 12/2010 | Perkins et al. |
| 2003/0126959 A1 * | 7/2003 | Khubani ............................ 81/64 |
| 2007/0089569 A1 * | 4/2007 | Hernandez ...................... 81/3.09 |

* cited by examiner

*Primary Examiner* — Bruce E Snow
*Assistant Examiner* — Melissa Hoban
(74) *Attorney, Agent, or Firm* — Joseph T Regard, Ltd plc

(57) ABSTRACT

A system for securing a residual limb having a sheath, thereabout and a strap emanating therefrom through the socket of a prosthetic limb or the like, utilizing a uniquely configured and operated lever which is specially designed for the task of pulling of the strap from the exterior of the socket to urge the residual limb therein. The system uses the tool, in pivotal communication with the prosthesis, to provide efficient pulling force with less effort, utilizing lever action. The preferred embodiment of the tool comprises an elongated body having specifically formed first and second ends, and has formed therethrough at least one passageway to receive the strap from the sock.

5 Claims, 3 Drawing Sheets

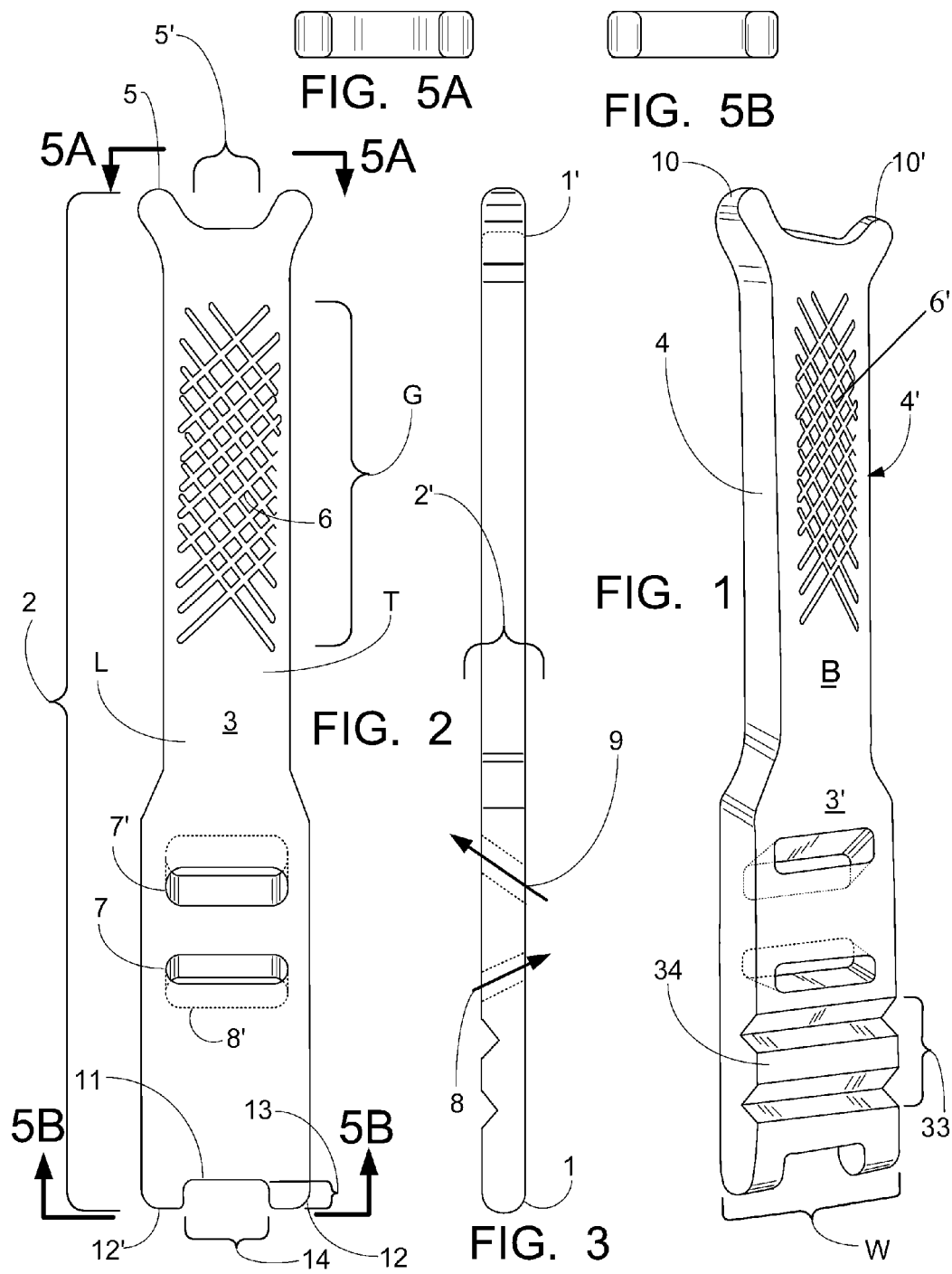

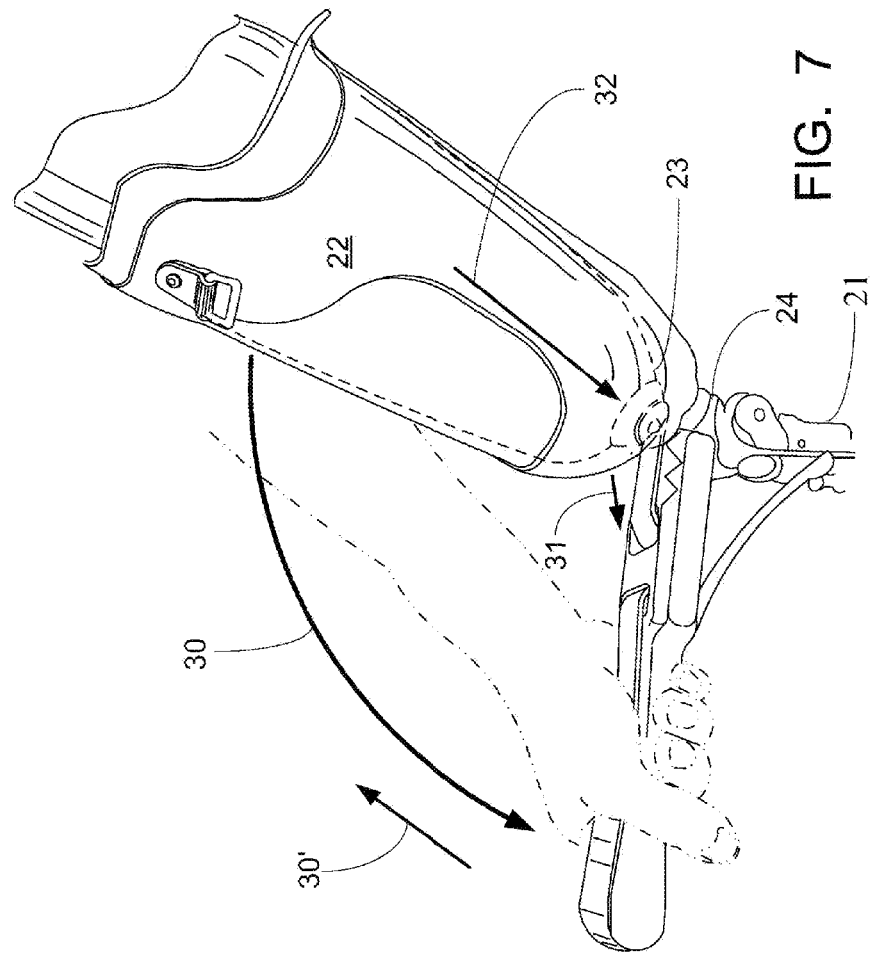
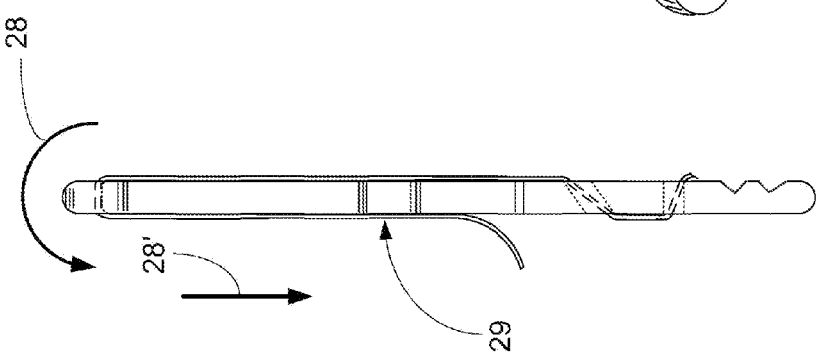
FIG. 6
FIG. 7

PROSTHETIC LIMB MOUNTING LEVER AND METHOD THEREFORE

TECHNICAL FIELD OF THE INVENTION

The present invention relates to method and apparatus to facilitate the proper placement of a user's residual limb into the socket or receiver of a prosthetic limb or the like. Specifically, the present invention provides an apparatus and method for pulling a strap or lanyard which is secured to a stocking, liner or the like about the residual limb, to facilitate the placement of said limb within the socket or receiver of the prosthetic limb.

BACKGROUND OF THE INVENTION

Although artificial or prosthetic limbs have been around for well over a century, much about them has not changed. The residual limb (also called the stump) of the user is generally secured to the prosthesis via a socket (also called the receiver) or the like engaging same. Straps have been used in the past to secure continued proper engagement of the residual limb to the prosthesis, but the straps can be uncomfortable and ineffective. Other systems have used a vacuum to retain the limb in place, but such a system only works as long as a good seal is in place, and variations in the size of the limb can result in loss of a seal.

It is believed the most popular means of facilitating the residual limb in the receiver of a prosthesis is by use of a tubular stocking or the like also called a "Jersey Sheath" "stump stocking", or "donning sock", which has generally been formed of elastic textile material which conforms to the residual limb and engages same when placed thereupon.

In use, a strap is provided at the end of the stocking. The stocking is pulled upon the residual limb to envelope the end of said limb and a length up said limb. A strap (also may be referenced as a lanyard) or the like is mounted to the end of the stocking at the end of the residual limb. The limb is placed into the socket and the free end of the strap is threaded through a slot, generally at the base of the socket, and the strap is then pulled to urge the residual limb (enveloped by the stocking) firmly into the base of the socket, where it is secured in place.

A problem with this system is that the wearer of the prosthetic limb may lack the strength, flexibility or dexterity to adequately pull the strap so as to properly secure the residual limb into the socket. Such users may be otherwise disabled, physically weak or lack the ability to firmly grasp the strap by hand.

Accordingly, various systems have arisen over the years to facilitate pulling of leg stocking with residual limb into the socket of the prosthesis, such as a cable and pulley system (U.S. Pat. No. 2,666,927), or a motorized, winch-like pulling apparatus (see U.S. Pat. No. 3,922,727 or 5,203,791), a roller system (U.S. Pat. No. 4,038,701), ratcheting mechanism (U.S. Pat. No. 5,326,351), or cable/spool system (U.S. Pat. No. 6,797,008).

A commonality of these systems is that they tend to be cumbersome, unnecessarily complicated, expensive, and have not been embraced by the public, Even today, it is believed that new wearers of these prosthetic limbs tend to be generally taught to use their hands in pulling the straps to urge the residual limb into the prosthetic socket, implicitly suggesting that the prior art systems were of limited usefulness.

Accordingly, there continues to exist a long felt, but unresolved need for a system for pulling a strap for a leg stocking for securing same into the socket of a prosthetic limb which is safe, effective, easy to use, and relatively inexpensive.

General Summary of Invention

The preferred embodiment of the present invention therefore provides a system for securing a residual limb having a sheath, sock or liner thereabout and a strap emanating therefrom to the socket of a prosthetic limb or the like, utilizing a uniquely configured and operated tool which is specially designed for the task of pulling of the strap from the socket to urge the residual limb therein.

The system uses the tool, in pivotal communication with the prosthesis, to provide efficient pulling force with less effort, utilizing lever action. The preferred embodiment of the tool comprises an elongated body having first and second ends, and has formed therethrough at least one passageway to receive the strap from the sheath.

The tool (held by the user) is formed to engage the strap of the sheath (which engages the residual limb) so as to pull the strap through a slot at the base of the prosthetic limb and urge said prosthetic socket firmly about the residual limb. In the preferred embodiment of the present invention, the strap passes through lower and upper strap slots formed in the tool, as well as about the distal end of the tool, and the tool and strap is grasped as the tool is pivoted at its free end, which has a slot or opening formed to engage the prosthesis (at the between the base of the socket and the prosthesis joint) as a pivot point, so as to tension the strap and urge the residual limb in place.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1 is an isometric view of the lever of the preferred embodiment of the present invention.

FIG. 2 is a front view of the lever of FIG. 1.

FIG. 3 is a side view of the lever of FIG. 1 showing the strap slots formed through the body in phantom.

FIG. 5A is a top, end view of the lever of FIG. 1, illustrating the slot formed therethrough for the passage of the strap thereabout.

FIG. 5B is a bottom, end view of the lever of FIG. 1, illustrating the slot formed therethrough for pivotally engaging the prosthesis to pull the strap, so as to urge the residual limb into place.

FIG. 6 is a side view of the lever of FIG. 1, showing in phantom the passage of the strap therethrough.

FIG. 7 is a side view of the lever of FIG. 1 being pivoted to pull the strap and urge the sheath and residual limb (in phantom) into the socket.

DETAILED DISCUSSION OF THE INVENTION

Figure 4:
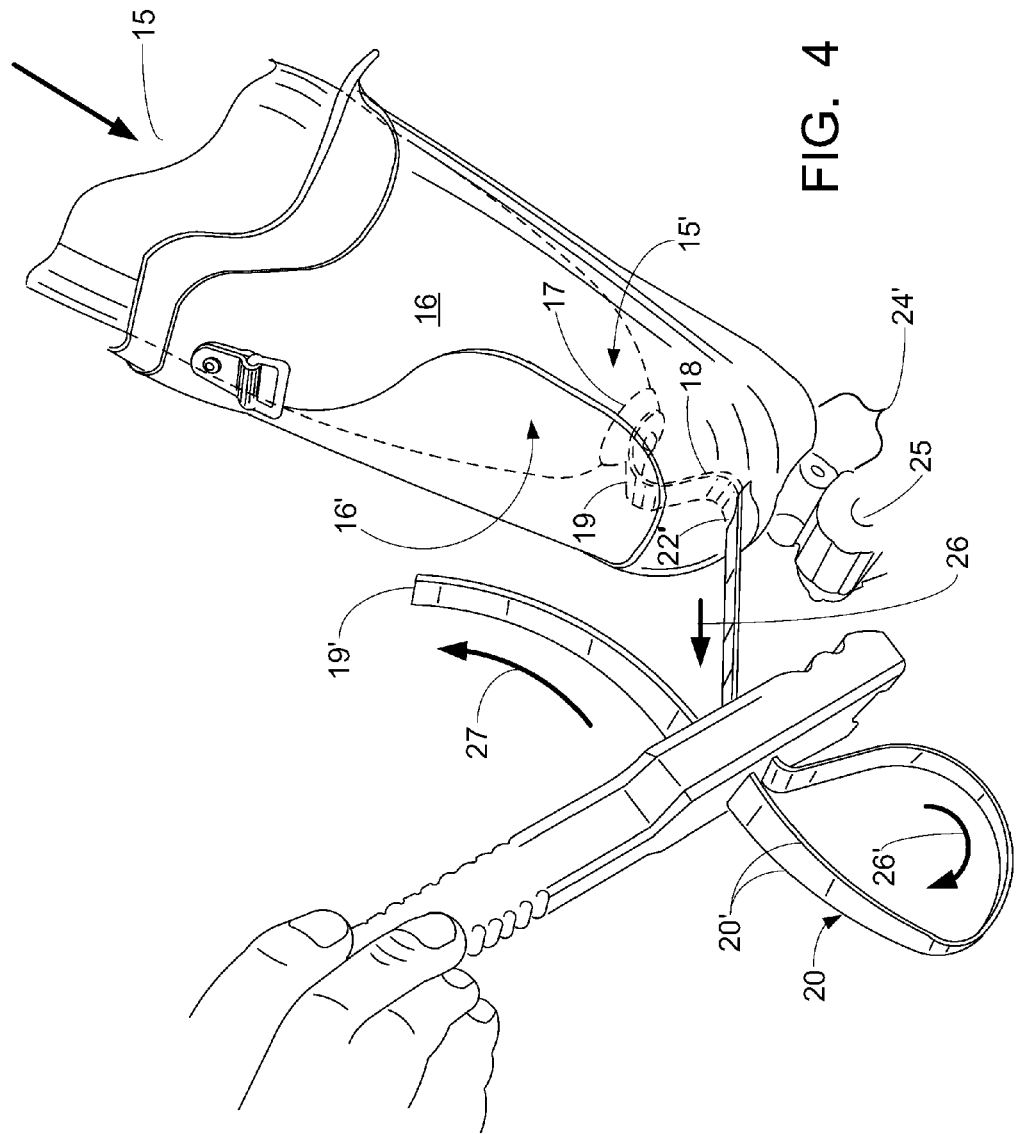
FIG. 4 is an isometric view of the lever of FIG. 1 having a strap from a sheath enveloping a residual limb (in phantom), said strap passing through the base of a socket of a prosthetic limb.

Referring to FIGS. 1-5B, the present invention comprises a tool T formed from a body B having a length 2, depth 2', width W, first 1 and second 1' ends, front 3 and rear 3' faces, and first 4 and second 4' sides. The preferred embodiment of the tool T is formed of a generally rectilinear body B having narrower width on associated with a gripping area G generally near the second end 1', the gripping area G having front 6 and rear 6' grips formed thereon to prevent slippage while in use. As will be shown, the grips are to engage a strap, and not the hand of the user, as would conventionally be the case.

Continuing with the Figures, in the vicinity of the first end 1 of the body are formed lower 7 and upper 7' slots. As shown, lower slot 7 has a width 8' and comprises a lateral 8 passage formed therethrough, communicating with said front 3 and rear 3' faces, respectively. A second, slot 9 is medially situated in parallel, spaced fashion above lower slot and is formed so as to provide an passage angled from the front face 3 so as to form an opening at said rear face 3' further from said lower slot 8 than said front face opening, and closer to said second end 1' than said front face opening.

Situated at the first 1 end of the body is a medially situated pivot recess 11 having a width 14 and depth 13, said pivot recess having first 12 and second 12' appendages on opposing sides of thereof, said first 12 and second 12' appendages extending from said first end 1 of said body along said first 4 and second 4' sides of body B, respectively.

Situated at said second 1' end of said body is a medially situated strap recess 5 having a width 5' and depth, said strap recess 5 first 10 and second 10' appendages extending from said second end 1' of said body along said first 4 and second 4' sides, respectively.

Referring to FIGS. 1-7 and particularly FIGS. 4-7, in use, a patient having a residual limb 15 having an end 15' places a stocking 16, generally formed of elastic textile material 16' (alternatively, silicone, or other flexible material having a frictional surface may be used), about the residual limb, such that a strap 18 having first 19 and second 19' ends emanates from the end 17 of stocking.

The residual limb 15 with stocking 16 is then placed in the socket 22 (may also be referenced as a receiver) of a prosthesis 21, the socket 22 having an open end for receiving the limb, and a closed end forming a base 23 having a slot 22' formed therethrough. The free end 19' of strap 18 is then threaded through slot 22' at the base 23 of prosthesis and the then pulled from socket via slot until resistance is met. Tool T is then positioned such that the first side 3 is facing toward the socket, with the first end 1 generally near the base 23 of the socket 22.

The free, second end 19' of strap 18 is then threaded 26 through the lower slot 7 at its rear face 3' opening, the strap then pulled 26 taught, the free, second end 19' of the strap then placed in the front face 3 opening of upper strap slot 7', then pulled 27 taught so as to provide a free length of threaded strap associated with the second end 19' of same.

The second end 19' of strap 18 is then laid flat against the rear face 3' of the tool, the strap length 20 then situated up to the second end 1' of the body, and over 28 the second end such that the width 20' of the strap is situated in strap slot 5 between the first 10 and second 10' strap slot appendages, the remaining free length of the strap then pulled taught 28', then laid flat 29 along the length of the gripping area 6 of the front face 3 of the body B of the tool T. The pivot slot 11 should now be positioned in contact with the connection point 24 between the base 23 of the socket and the pivotally adjustable joint 25, with the pivot slot appendages 12, 12' of the first end of the tool ideally situated about the width 24' of the connection point 24.

Referring to FIGS. 1-7, in use, the user grasps the gripping area of the tool, squeezing the strap against both the opposing grip areas 6, 6', and simultaneously pivoting the lever with strap from the second end of the tool being adjacent to the socket, to the second end being urged away from the socket, with the first end pivotally engaging the connection point 24 below socket, so as to pull 31, via lever action, the strap out of prosthesis slot 22', pulling stocking 16 clad residual limb into the socket.

This procedure can be repeated with the tool, that is, the tool pivoted back 30' to its prior position with the second end adjacent to the socket, the strap pulled through the upper and lower slots to and realigned along the tool as discussed above so that the slack is removed, the hand tripping the straps at the gripping area of the tool then pivoting 30 same again, again urging or pulling 31 the stocking 16 clad residual limb deeper into the socket, until it is in place in the socket. The strap exterior the socket is then removed from the tool and stowed utilizing whatever system is provided for that particular prosthesis. Teeth 33 formed along the rear face near the first end of the device may be provided to provide a gripping surface to engage a prosthesis, especially having a base which does not engage the pivot recess 11 of the first end of the device in an ideal fashion.

It is noted that the design of the tool may vary depending upon the particular prosthesis the tool is to work with, so as to optimize interface with same and enhance the efficiency of pulling the strap with the least amount of effort and trouble.

For example, the pivot recess 11 may vary in width, depth or configuration to best suit its pivotal engagement with the prosthesis it is to be used with. In the present example, the pivot recess has a width, depth and configuration to best engage connection point 24 below the base of the socket on the prosthesis. Further, the optimal pivot point may vary depending upon the configuration of the prosthesis, the location of the slot formed through the prosthesis slot, etc.

Further, the length, width, depth, or other attribute may vary for the present tool depending upon the user's requirements and capabilities.

ELEMENTS OF THE INVENTION

T tool
B body
L lever
W width
G gripping area
1,1' first, second ends
2,2' length, depth
3,3' front, rear faces
4,4' first, second sides
5,5' strap recess, width
6,6' grip areas
7,7' lower, upper strap slots
8, 8' lower slot angled from lower rear face, upward toward first end, width
9 upper slot angled from lower front face, upward toward first end, rear face
10,10' first, second strap slot appendages
11 prosthesis
12,12' first, second pivot slot appendages
13, 13' depth of strap slot, pivot slot
14 width of pivot slot
15, 15' residual limb, end
16, 16' stocking of elastic textile material, silicone or other flexible material which can frictionally engage limb.
17 stocking end
18 strap
19,19' strap ends
20,20' strap length, width
21 prosthesis
22,22' prosthesis socket, slot 23 base of prosthesis socket
24, 24' connection point, width
25 joint
26 threaded
27 pulled
28 free length of threaded strap, pulled
29 strap positioned along front face.
30,30' pivot, retract
31 pull
33 teeth
34 ridges
- - -

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A method of urging a residual limb of a user into a receiver of a prosthesis, the receiver having an open end for receiving the residual limb and a closed end, the receiver having a slot formed through the receiver and situated in the vicinity of said closed end, the residual limb having a stocking engaged thereto having a strap having a free end emanating therefrom, said method comprising the steps of:
   a) providing a tool having:
      i. a length, front and rear faces, and first and second ends;
      ii. said tool having a first slot formed through said front and rear face, said first slot formed to allow the passage of a length of said strap therethrough;
      iii. said first end of said tool formed to pivotally engage said prosthesis;
      iv. said second end of said tool formed to retain said strap;
   b) placing said free end of said strap through said slot formed through said receiver;
   c) positioning said front face of said tool in the vicinity of said slot formed through said receiver, with said first end of said tool situated adjacent to the closed end of said receiver;
   d) threading said free end of said strap at said front face through said first slot and pulling said strap until resistance is met;
   e) aligning the length of said strap along one of said front or rear faces of said tool, over said second end of said tool, and over the other of said front or rear faces of said tool respectively;
   f) gripping said tool over said length of said strap along said tool, while positioning said first end of said tool against said prosthesis; and
   g) pivoting said second end of said tool away from said receiver so as to pull said strap out of said receiver via said strap slot, urging said residual limb into said receiver.

2. The method of claim 1, wherein after step (g) there is provided the further steps of:
   h) pivotally repositioning said second end of said tool adjacent to said receiver, providing slack in said strap between said tool and said receiver;
   i) releasing said grip of said tool and pulling said free end of said strap to remove said slack in said strap;
   j) repeating steps f)-g).

3. The method of claim 1, wherein said method further comprises:
   after claim 1, step ii., the added step of:
      ii(a) providing a second slot spaced towards said second end of said tool relative to said first slot, said second slot for receiving said strap therethrough after said strap has been threaded through said first slot;
   and after claim 1, step iv, the added step of:
      v. wherein said front and rear faces are situated in the vicinity of said second end of said tool, and form a gripping area having a gripping surface, upon pivoting said tool;
   and after step d), the added step of:
      d1) threading said free end of said strap at said rear face through said second slot and pulling until resistance is met;
   and in step g) there is added the additional step of:
      g1) while allowing said first and second slots to provide frictional resistance to prevent said strap from slipping providing tension; and
      h) pivotally repositioning said second end of said tool pivotally back to said receiver so as to release tension to provide slack in said strap.

4. A method of urging a residual limb of a user into a receiver of a prosthesis, the receiver having an open end for receiving the residual limb and a closed end, the receiver having a slot situated in the vicinity of said closed end, the residual limb having a stocking engaged thereto having a strap having a free end emanating therefrom, said method comprising the steps of:
   a) providing a tool having:
      i. a length, front and rear faces, and first and second ends;
      ii. said tool having a first slot formed through said front and rear face, said first slot formed to allow the passage of a length of said strap therethrough;
      iii. a second slot spaced towards said second end of said tool relative to said first slot, said second slot for receiving said strap therethrough after said strap has been threaded through said first slot;
      iv. said front and rear faces situated in the vicinity of said second end of said tool forming a gripping area having a gripping surface, upon pivoting said tool;
   b) placing said free end of said strap through said slot formed through said receiver;
   c) positioning said front face of said tool in the vicinity of said slot formed through said receiver, with said first end of said tool situated adjacent to the closed end of said receiver;
   d) threading said free end of said strap at said front face through said first slot and pulling same until resistance is met;
   e) threading said free end of said strap at said rear face through said second slot and pulling until resistance is met;
   f) aligning the length of said strap along said front face of said tool, over said second end of said tool, and over said rear face of said tool respectively;
   g) gripping said tool over said length of said strap along said gripping area of said tool, while positioning said first end of said tool against said prosthesis; and
   h) pivoting said second end of said tool away from said receiver so as to pull said strap out of said receiver via said strap slot, urging said residual limb into said receiver, while allowing said first and second slots to provide frictional resistance to prevent said strap from slipping, providing tension;
   i) pivotally repositioning said second end of said tool pivotally back to said receiver so as to release tension to provide slack in said strap.

5. The method of claim 4, wherein after step (i) there is provided the further steps of:
   j) releasing said grip of said tool and pulling said free end of said strap to remove said slack in said strap;
   k) repeating steps g)-i).

* * * * *